United States Patent [19]
Theeuwes et al.

[11] Patent Number: 4,976,966
[45] Date of Patent: Dec. 11, 1990

[54] DELAYED RELEASE OSMOTICALLY DRIVEN FLUID DISPENSER

[75] Inventors: Felix Theeuwes, Los Altos; Patrick S. L. Wong, Palo Alto, both of Calif.

[73] Assignee: ALZA Corporation, Palo Alto, Calif.

[21] Appl. No.: 291,725

[22] Filed: Dec. 29, 1988

[51] Int. Cl.$^5$ ................................................ A61K 9/20
[52] U.S. Cl. ..................... 424/473; 424/408; 424/422; 424/423; 664/892.1
[58] Field of Search ............. 604/892.1; 424/449, 424/473, 464, 465, 408

[56] References Cited

U.S. PATENT DOCUMENTS

| | | | |
|---|---|---|---|
| 3,732,865 | 5/1973 | Higuchi et al. | 604/892.1 |
| 3,760,804 | 9/1973 | Higuchi et al. | 604/892.1 |
| 3,760,984 | 9/1973 | Theeuwes | 222/95 |
| 3,865,108 | 2/1975 | Hartop | 128/260 |
| 3,987,790 | 10/1976 | Eckenhoff et al. | 128/260 |
| 3,995,631 | 12/1976 | Higuchi et al. | 128/260 |
| 3,995,632 | 12/1976 | Nakano et al. | 604/892.1 |
| 4,034,756 | 7/1977 | Higuchi et al. | 128/260 |
| 4,207,893 | 6/1980 | Michaels | 128/260 |
| 4,320,758 | 3/1982 | Eckenhoff et al. | 604/892.1 |

*Primary Examiner*—Thurman K. Page
*Attorney, Agent, or Firm*—D. Byron Miller; Edward L. Mandell; Steven F. Stone

[57] ABSTRACT

An osmotically driven pump is provided that is capable of being miniaturized to a size suited for swallowing or implanting in an animal. The pump may be used to administer a drug in fluid form after an initial activation period during which substantially no drug is administered. The basic components of the pump are a shaped semipermeable membrane that encapsulates an osmotically effective solute and preferably a drug or other beneficial agent and a discharge port through which the drug or other beneficial agent is dispensed. A semipermeable or microporous outer cover surrounds the semipermeable membrane and seals it from an external aqueous environment. A water-swellable composition is operatively positioned between the end of the semipermeable membrane and the outer cover. Preferably, a water wicking layer at least partially surrounds the semipermeable membrane and is also sealed within the outer cover. In operation, the pump is placed in an aqueous environment. Water from the environment passes through the semipermeable/microporous portion of the outer cover into the water-swellable composition. The water-swellable composition absorbs water, expands, and in piston-like fashion displaces the outer cover, thereby exposing the semipermeable membrane to the aqueous environment and activating the osmotic pump. The time required for the water-swellable composition to absorb water, expand and displace the outer cover provides an initial activation period during which substantially no drug is delivered by the pump.

38 Claims, 2 Drawing Sheets

DELAYED RELEASE OSMOTICALLY DRIVEN FLUID DISPENSER

BACKGROUND OF THE INVENTION

1. Field of the Invention

The invention relates to an osmotically driven fluid dispenser which is activated after being exposed to an aqueous environment. The dispenser can be programmed to begin delivering a fluid, such as a drug solution or a drug suspension, after a predetermined delay period following introduction of the dispenser into the aqueous environment.

2. Description of the Prior Art

The present invention provides an improved osmotically driven fluid dispenser of the type described in commonly owned U.S. Pat. Nos. 3,987,790; 3,995,631 and 4,034,756. These patents describe mini-osmotic pumps. Mini-osmotic pumps generally comprise a semipermeable wall which encloses either an osmotic solute or a combination of an osmotic solute and a beneficial agent such as a drug. An orifice is provided through the semipermeable wall. When the pump is placed in a aqueous environment, water permeates through the wall and dissolves the osmotic agent and/or beneficial agent. The solution of the osmotic agent and/or beneficial agent is then pumped through the delivery orifice as fresh incoming water enters the pump.

The mini-osmotic pumps disclosed in the three above-identified U.S. Patents separate the osmotically effective solute from the drug. The pumps disclosed in these patents additionally include an inner flexible bag that holds the drug charge. The osmotically effective solute composition (e.g., an inorganic salt) is present as an intermediate layer encapsulating the bag. The outer shape-retaining membrane is at least in part permeable to water and encapsulates both the layer of osmotically effective solute composition and the bag. A plug seals the open end of the bag, and a filling/discharge port in the plug communicates with the interior of the bag.

In operation the bag is filled with drug solution via the filling/discharge port and placed in an aqueous environment, such as a body cavity or within body tissue. Water is imbibed from the environment by the osmotically effective solute through the membrane into the space between the inner flexible bag and the membrane. Since the bag is flexible and the membrane is rigid, the imbibed water squeezes the bag inwardly, thereby displacing drug out the filling/discharge port.

Generally, the mini-osmotic pumps of the prior art are activated upon exposure to an aqueous environment. The pumps begin dispensing their contents after water from the environment has permeated through the outer semipermeable membrane. Thus, any delay between the time when the mini-osmotic pump is placed in an aqueous environment and the time when the pump begins dispensing its contents is determined primarily by one or more of the following parameters: (1) the permeation characteristics of the semipermeable membrane; (2) the thickness of the semipermeable membrane; (3) any exterior coating on the semipermeable membrane; (4) the composition of the osmotically effective solute and its osmotic imbibition properties; and (5) the mechanical properties of the drug/osmotic agent reservoir.

Unfortunately, designing a pump with a pre-programmed drug delivery activation period based on one or more of the five above listed properties has proven to be disadvantageous from several respects. For example, in order to "program" a pump to begin dispensing drug after an initial activation period (e.g., a period of delay between the time when the pump is first placed in an aqueous environment and the time when the pump begins dispensing drug), pump designers have attempted to vary one or more of the physical properties of the semipermeable membrane wall. Unfortunately, while the semipermeable membrane wall properties do control the rate at which beneficial agents are dispensed from the pump, they do not provide much control over the initial activation period. For example, one can utilize a relatively impermeable membrane which only allows water to permeate through the pump wall very slowly. Unfortunately, this design severely restricts the rate at which the drug is dispensed from the device after the initial activation period. Another method of preprogramming the pump to begin delivering drug after an initial activation period is to increase the thickness of the outer semipermeable membrane. Unfortunately, this presents serious size limitations on the device, in particular when working with pumps of a size suited for swallowing or implanting in an animal or the human body.

One can also utilize an osmotic solute composition which only generates a low osmotic pressure gradient across the membrane, thereby causing water to permeate through the membrane at a very slow rate. Unfortunately, this design has very little effect on the initial activation period and also severely restricts the rate at which the drug is dispensed from the device after the initial activation period.

Finally, one can coat the semipermeable outer membrane of the pump with a bioerodible polymer. After the polymer erodes, the semipermeable membrane becomes exposed to the exterior aqueous environment. Unfortunately, it is very difficult to precisely control the rate at which a bioerodible polymer layer erodes. Furthermore, bioerodible polymers generally have the property of allowing a certain amount of water to be transported therethrough before they are fully eroded. This early water transport results in the pump dispensing a certain amount of drug or other beneficial agent before the desired activation period has fully expired.

Thus, there has been a need in the art for a mini-osmotic pump which can be "programmed" to deliver substantially no drug during a predetermined activation period and yet which can begin delivering the drug at a pharmaceutically acceptable rate after the initial activation period.

SUMMARY OF THE INVENTION

The present invention provides a mini-osmotic pump, and a method of using same. The pump comprises an improved osmotically driven fluid dispenser which can be programmed to begin dispensing a fluid, such as a drug charge, after a predetermined activation period. In its broadest sense, the dispenser comprises a shaped membrane defining a compartment. The compartment contains an osmotically effective solute composition. The membrane is, at least in part, permeable to water. The dispenser has a delivery port from which a solution of the solute may be dispensed from the compartment. The dispenser also comprises (1) a cover sealing the membrane from an exterior aqueous environment, at least a portion of the cover being comprised of a semipermeable or microporous material, and (2) a water-swellable composition operatively positioned within the cover. The water-swellable composition is capable of absorbing water which passes through the semipermeable/microporous portion of the cover, expanding over a predetermined activation period, displacing the cover and thereby exposing the membrane to the aqueous environment. Preferably, the dispenser also includes a wicking layer surrounding the semipermeable membrane and initially sealed within the outer cover. The wicking layer wicks water from the aqueous environment to the surface of the membrane and causes a more pronounced increase in the beneficial agent delivery rate profile, from substantially no agent delivery to substantially maximum agent delivery (as opposed to a more gradual increase in the agent/drug delivery rate over time).

In one embodiment of the invention, the dispenser includes an inner flexible bag adapted to contain the fluid to be dispensed, an intermediate layer of an osmotically effective solute composition at least partly encapsulating the bag, and a shape-retaining membrane encapsulating the layer of osmotically effective solute composition. The membrane is at least in part permeable to water. A port extends from the interior of the bag to the exterior of the dispenser through which the fluid may be charged into the bag and dispensed from the bag. The dispenser also comprises: (1) a cover sealing the membrane from an exterior aqueous environment, at least a portion of the cover being comprised of a semipermeable or microporous material and (2) a water-swellable composition operatively positioned within the cover. The water-swellable composition is capable of absorbing water which passes through the semipermeable/microporous portion of the cover and expanding over a predetermined activation period in response thereto. In operation, the expanding water-swellable composition displaces the cover, thereby exposing the membrane to the aqueous environment and activating the dispenser. Preferably, the osmotically driven fluid dispenser also includes a wicking layer surrounding the semipermeable membrane and sealed within the outer cover. When the outer cover is displaced by the water-swellable composition, the wicking layer becomes exposed to the exterior aqueous environment and wicks water therefrom to the surface of the semipermeable membrane. The wicking layer causes a more pronounced increase in the beneficial agent release profile, from substantially no agent delivery to substantially maximum agent delivery (as opposed to a more gradual increase in the agent/drug delivery rate over time).

The present invention also includes a method of activating an osmotically driven fluid dispenser after an initial activation period. The fluid dispenser includes a shaped membrane defining a compartment. The compartment contains an osmotically effective solute composition. The membrane is at, least in part, permeable to water. The dispenser has a delivery port from which a solution of the solute may be dispensed from the compartment. In its broadest sense, the method comprises the steps of (1) sealing the membrane within a cover which is comprised, at least in part, of a semipermeable or microporous material, (2) positioning a water-swellable composition within the cover, said water-swellable composition being capable of absorbing water which passes through the semipermeable/microporous portion of the cover and expanding over a predetermined activation period in response thereto, and (3) exposing the cover to an aqueous environment, whereby said water-swellable composition absorbs water from the environment, expands and displaces the cover, thereby exposing the membrane to the aqueous environment and activating the dispenser. Preferably, the method also includes the step of positioning a wicking layer between the membrane and the cover. The wicking layer is initially sealed within the cover but is later exposed to the aqueous environment after the cover has been displaced. The wicking layer functions to wick water from the aqueous environment to the surface of the membrane. The wicking layer causes a more pronounced increase in the beneficial agent release profile, from substantially no agent delivery to substantially maximum agent delivery (as opposed to a more gradual increase in the agent/drug delivery rate over time).

BRIEF DESCRIPTION OF THE DRAWINGS

Like numerals refer to like parts in the various figures.

DETAILED DESCRIPTION OF THE INVENTION

Figure 1:
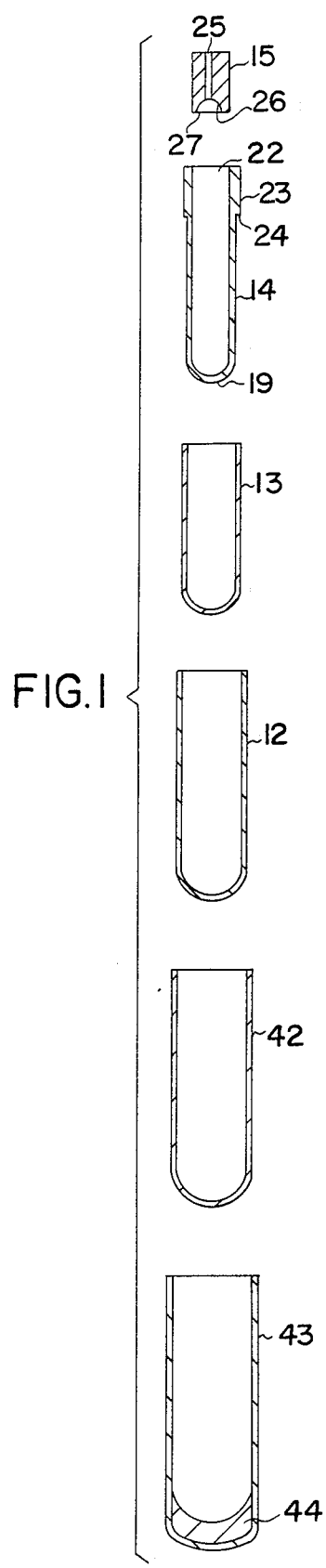
FIG. 1 is an elevational, exploded, sectional view of a preferred embodiment of the dispenser of the present invention.
Figure 2:
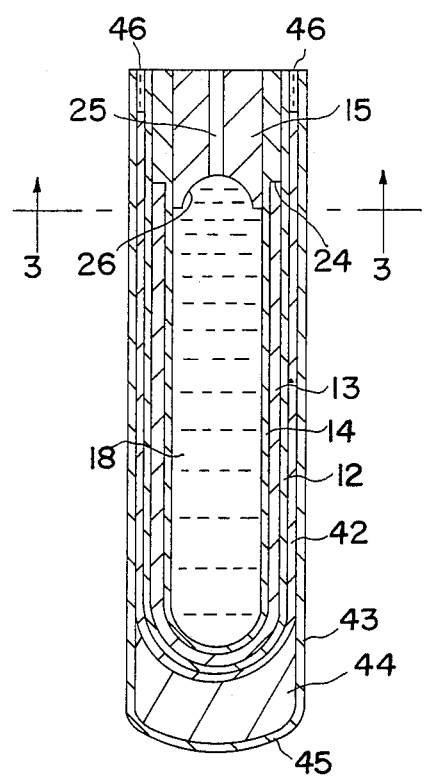
FIG. 2 is an enlarged sectional view of the dispenser of FIG. 1, prior to its introduction into an aqueous environment.
Figure 3:
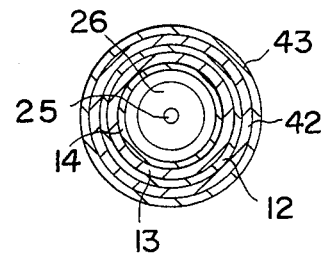
FIG. 3 is a sectional view of the dispenser of FIGS. 1 and 2 taken along line 3—3 of FIG. 2.
Figure 4:
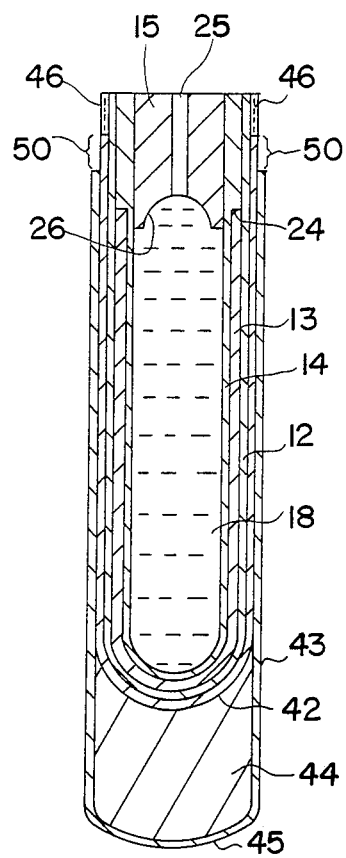
FIG. 4 is an enlarged sectional view of the dispenser of FIG. 2 after it has been introduced into an aqueous environment and with its water-swellable composition 44 in an expanded condition.
Figure 5:
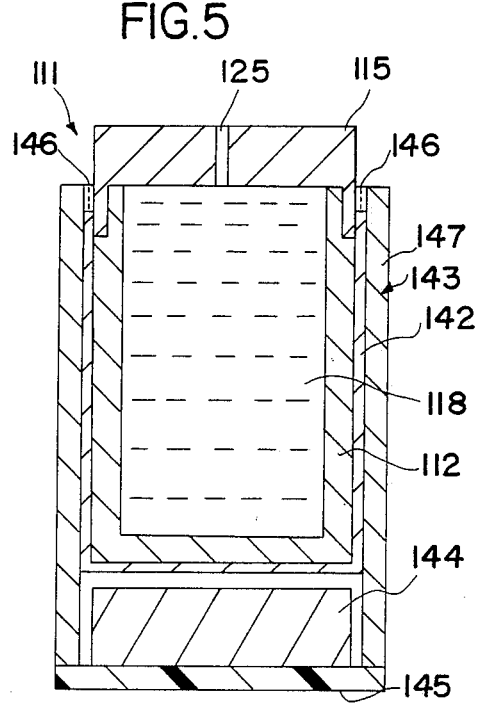
FIG. 5 is a sectional view of another embodiment of the dispenser of the present invention, prior to its introduction into an aqueous environment.
Figure 6:
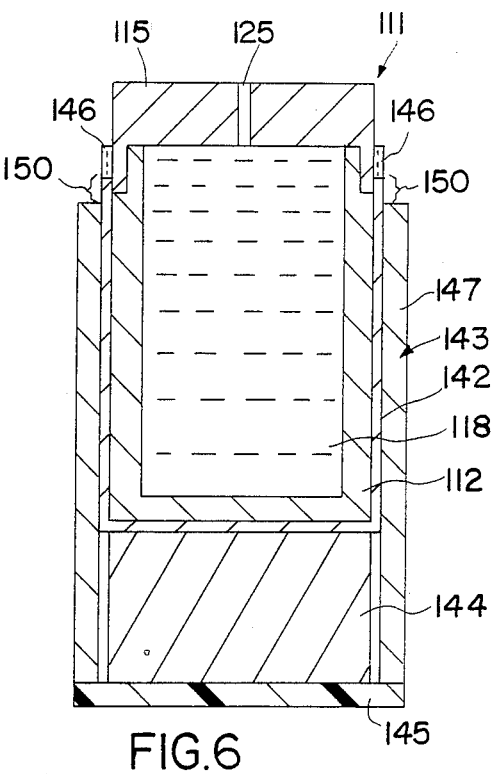
FIG. 6 is a sectional view of the dispenser of FIG. 5 after it has been introduced into an aqueous environment and with its water-swellable composition 144 in an expanded condition.

The drawings illustrate an osmotically driven fluid dispenser, generally designated 11 in FIGS. 1–4 and 7, and designated 111 in FIGS. 5 and 6. As shown in FIGS. 1 and 2, dispenser 11 comprises a mini-osmotic pump such as that described in U.S. Pat. No. 4,320,758 with the additional elements of (i) a shape-retaining semipermeable or microporous outer cover 43 surrounding the mini-osmotic pump and isolating the semipermeable membrane 12 from the environment; and (ii) a water-swellable composition 44 positioned between the closed end 45 of the outer cover 43 and the mini-osmotic pump. Preferably, the pump of the present invention also includes a third additional element comprising a wicking layer 42 at least partially surrounding the semipermeable membrane 12.

Figure 7:
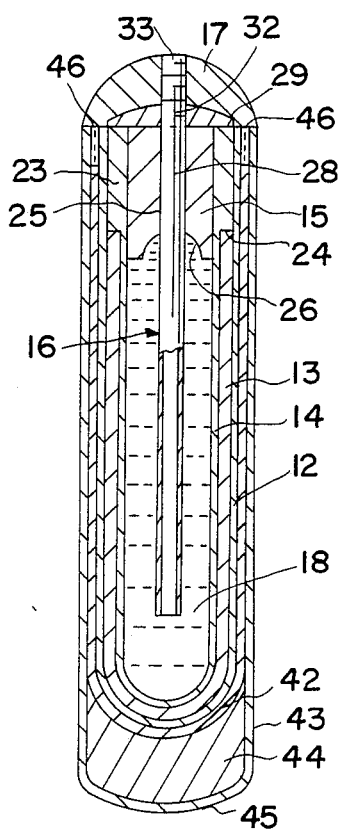
FIG. 7 is a sectional view of the dispenser illustrated in FIGS. 1 and 2 with an optional flow moderator in accordance with another preferred embodiment of the invention.

The basic components of the mini-osmotic pump are a shape-retaining semipermeable and/or microporous membrane 12; an intermediate osmotic layer 13 which, as shown in the illustrated embodiment, is preferably a thermoformed sleeve made from a dispersion of an osmotically effective solute in a water soluble thermoplastic polymer matrix; an inner flexible bag 14; and an impermeable plug 15 having a filling/discharge port 25. Optionally, as shown in FIG. 7, the mini-osmotic pump may also contain a flow moderator 16 comprising a tube 28, a head 29 and a flow moderator cap 17.

As mentioned above, a water wicking layer 42 is preferably disposed around the exterior of membrane 12. In the preferred embodiment illustrated in FIGS. 1-3, wicking layer 42 substantially completely surrounds membrane 12. However, it is within the scope of the present invention to utilize no wicking layer, or to utilize a wicking layer 42 which wicks water to only a portion of the exterior surface of membrane 12 or to utilize an open space between membrane 12 and cover 43 which draws in water by capillary action.

Prior to introduction into an aqueous environment, the dispenser 11 has the configuration illustrated in FIG. 2. In this configuration, the cover 43 completely surrounds the semipermeable membrane 12 and the wicking layer 42. An annular plug 46 of a suitable sealant, such as sealing wax, is placed between the upper end of membrane 12 and outer cover 43 as best shown in FIG. 2. Plug 46 in combination with outer cover 43 sealing isolates both the wicking layer 42 and the semipermeable membrane 12 from the external aqueous environment.

As is shown in FIGS. 1, 2 and 4, dispenser 11 includes a water-swellable composition 44 positioned between the end portion 45 of outer cover 43 and the lower end of the mini-osmotic pump. Composition 44 absorbs water which permeates through the outer cover 43 and swells in response thereto. Composition 44 must be able to swell enough to displace the outer cover 43 and expose at least a portion 50 of the wicking layer 42 to the aqueous environment, as best shown in FIG. 4. Examples of water-insoluble, water-swellable compositions that may be used in composition 44 are disclosed in U.S. Pat. No. 3,865,108 at col. 2, lines 35-50 and in U.S. Pat. No. 4,207,893 at col. 4, lines 23 to 47, the disclosures of which are incorporated herein by reference. Preferably, composition 44 consists essentially of polyethylene oxide having a molecular weight in the range of about 100,000 to about 4,000,000. Preferably, the water-swellable composition 44 is slightly cross-linked to limit the degree of swelling of composition 44 and thereby limit the maximum length of device 11 in its extended condition. This is particularly important when device 11 is to be either ingested or implanted within an animal body. Cross-linking of composition 44 may be achieved by conventional means such as by mixing hydrophilic polymers, via hydrogen or ionic bonding, by blending hydrophilic and hydrophobic polymers, or by controlled irradiation of the polymer composition using either radio isotopes or an ionized beam.

Those skilled in the art will recognize that the water-swellable composition 44 provides an initial delay between the time that the device 11 is first introduced into a aqueous environment and the time when a portion of wicking layer 42 is first exposed to the external aqueous environment. This delay is responsible for the initial activation period, after which membrane 12 becomes wetted and device 11 begins to dispense fluid 18 in a known manner. The activation period can be adjusted by varying the amount and composition of the water-swellable composition 44. For example, the osmotic activity of the water-swellable composition 44 and the water permeability characteristics of the semipermeable cover 43 can be adjusted according to known principles. These factors can be varied to adjust the duration of the initial activation period of the dispenser.

Dispenser 11 operates in the following manner. Once placed in an aqueous environment, such as within a body cavity or within body tissue, water from the environment is imbibed by the water-swellable composition 44 through semipermeable cover 43. The cover 43 may be comprised entirely of a semipermeable or microporous material, but preferably only the end portion 45 is comprised of a semipermeable or microporous material with the remainder of cover 43 being comprised of a water impermeable material. In the preferred configuration, water is transported only through end portion 45 directly into composition 44, without allowing wicking layer 42 to become wetted. As the composition 44 absorbs water, it begins to swell. Since the cover 43 is shape-retaining, the swelling of composition 44 displaces the outer cover 43, causing it to slide over the wicking layer 42. Preferably, the portions of cover 43 immediately adjacent the wicking layer 42 are water impermeable so that during the period of time in which composition 44 is absorbing water and swelling, the wicking layer remains completely dry. Eventually, the composition 44 swells a sufficient amount to break the seal provided by the wax plug 46 and exposes a portion 50 of wicking layer 42 to the aqueous environment. Once exposed, the wicking layer 42 wicks water to substantially the entire surface of membrane 12. Water from the wicking layer 42 is imbibed by the solute of sleeve 13 through membrane 12 at a rate determined by the osmotic activity of the solute, and the osmotic reflection coefficient, and the composition, thickness, and the wetted area of membrane 12. The imbibed water causes the volume of layer 13 to increase. Since membrane 12 is shape-retaining, the imbibed water generates hydraulic pressure on the exterior of bag 14 causing bag 14 to be squeezed inwardly. This squeezing forces fluid 18 out of the dispenser 11 through port 25. As indicated, fluid 18 may be an active agent composition. In such instances the dispenser 11 will discharge active agent directly. Alternatively fluid 18 may be inert and the dispenser may be used simply as a displacement pump. In this alternative the dispenser is suitably interconnected by well known means to a reservoir of the fluid (active agent) to be discharged, such that the inert fluid displaces the fluid active agent from the reservoir in a predetermined regimen to the desired administration site. Such alternatives are particularly attractive in instances in which the fluid active agent is incompatible with bag 14.

The wicking layer 42 may be composed of any material which is effective to absorb water from the aqueous environment and distribute the water along the surface of membrane 12. Examples of suitable materials include cellulosic papers and fabrics, either woven or nonwoven, containing fibers made from cotton, wool and similar hydrophilic materials. Particularly preferred are hydrophilic polymers (e.g., cellulose acetate) which can be simply applied as a coating on the surface of membrane 12. The wicking layer 42 is attached to the exterior of membrane 12 by conventional means such as a frictional fit, a hydrophilic glue (e.g., cellulose acetate glue) or by melt bonding the wicking layer 42 to the membrane 12. The wicking layer 42, once wetted, also serves to decrease the sliding friction between the outer cover 43 and the membrane 12.

Preferably, the wicking layer 42 completely surrounds the exterior of membrane 12 and is in intimate contact therewith. In this way, when the portion 50 of wicking layer 42 is exposed to the exterior aqueous environment, the entire surface of semipermeable membrane 12 becomes wetted due to the wicking action of layer 42. In this way, the rate at which fluid 18 is dispensed from dispenser 11 is independent of the surface area of portion 50 exposed by displacing cover 43. Furthermore, a more pronounced increase in the agent delivery rate is attained since the entire surface of membrane 12 is available for fluid transport. On the other hand, when no wicking layer 42 is used, the rate at which fluid 18 is dispensed from dispenser 11 will be dependent upon a number of factors but primarily upon the area of membrane 12 exposed to the aqueous environment by the displaced cover 43.

As an alternative to the wicking layer 42, one can provide a small gap between the membrane 12 and the sleeve 43 using appropriate spacers (not shown in the drawings). The spacers maintain a small gap between membrane 12 and sleeve 43, both before and after the outer sleeve 43 has been displaced. In this way, water from the exterior environment is drawn into the gap by capillary action after the wax seal is broken, thereby wetting the entire surface of the membrane 12.

The slidable outer cover 43 is illustrated in the figures as cylindrical but could also have other shapes. Cover 43 is preferably shape-retaining, that is, it is sufficiently rigid to be substantially undeformed by the swelling of composition 44. Cover 43 may be semipermeable, microporous or a combination of the two. In any event, at least a portion of cover 43 should be permeable to water and substantially impermeable to composition 44. Examples of polymers that may be used to make permeable cover 43 are cellulose esters and ethers such as cellulose acetate and cellulose butyrate and the other semipermeable film-forming compositions disclosed in U.S. Pat. No. 3,760,984 at col. 4, line 53 to col. 5, line 39 and in U.S. Pat. No. 3,995,631 at col. 7, line 40 to col. 8, line 15, the disclosures of which are incorporated herein by reference.

Bag 14 is adapted to contain a fluid composition, such as an active agent composition 18 (FIG. 2) in fluid form. The term "active agent" as used herein means any compound or mixture of compounds that can be dispensed to produce a predetermined beneficial and useful result. Active agents include pesticides, germicides, biocides, algicides, rodenticides, fungicides, insecticides, antioxidants, plant growth promoters, plant growth inhibitors, preservatives, surfactants, disinfectants, sterilization agents, catalysts, chemical reactants, fermentation agents, cosmetics, foods, nutrients, food supplements, drugs, vitamins, sex sterilants, fertility inhibitors, fertility promoters, air purifiers, microorganism attenuators, and other compositions that benefit the environment, surroundings, and habitat, including animals and humans. In the preferred embodiment the active agent is a drug that produces a local or systemic physiologic or pharmacologic response when administered to animals or humans.

In order to be a suitable container for the fluid, bag 14 should be substantially impermeable to the fluid composition and be compatible with the composition. By "compatible", it is meant that the bag should not be corroded, solubilized, or otherwise affected deleteriously by the composition. Additionally, when the composition is a drug, the composition should not be significantly contaminated by the bag, such as by the extraction of leachables from the material forming the bag. Bag 14 may be made from elastomeric compositions formed into thin sheets. The elastomeric properties and the thickness of the bag wall should be such as to cause the bag to readily collapse inwardly when a force is applied to the bag exterior. Such elastomeric compositions are disclosed in commonly owned U.S. Pat. No. 3,760,984 at col. 5, line 40 to col. 7, line 37 and in commonly owned U.S. Pat. No. 3,995,631 at col. 8, lines 14–32 which disclosures are incorporated herein by reference.

Bag 14 is elongated and generally cylindrical and is closed at its end 19 and open at its opposite end 22. The bag wall is thickened outwardly at 23 to form a shoulder 24. As seen in FIG. 2 the portion of the exterior of bag 14 below shoulder 24 is encapsulated by sleeve 13 whose wall is approximately as thick as shoulder 24 is wide.

Bag 14 is surrounded by a layer 13 of an osmotically effective solute. The purpose of layer 13 is to imbibe water across membrane 12 into the space between the exterior bag 14 and the inner surface of membrane 12, that is, the space occupied by layer 13. Osmotically effective solute compositions that may be used to form layer 13 are disclosed in U.S. Pat. No. 3,760,984 at col. 7, line 38 to col. 8, line 2 and in U.S. Pat. No. 3,995,631 at p. 11, line 65 to col. 12, line 3 and col. 14, lines 20–28, which disclosures are incorporated herein by reference.

In a preferred embodiment of the present invention, sleeve 13 is made from a thermoformable osmotically effective solute composition. The components of the composition are a water soluble, thermoplastic polymer vehicle and one or more of the osmotically effective solutes mentioned above. The purpose of the solute is to imbibe water from the wicking layer 42 (or from the exterior environment when no wicking layer 42 is used) across membrane 12 into the space between the exterior of bag 14 and the inner surface of membrane 12, that is, the space occupied by sleeve 13. The osmotic pressure of the solute when in solution should be significantly greater than the osmotic pressure of the liquid of the environment. In dispensers that are to be ingested by or placed within an animal, the osmotic pressure of the solute solution must exceed the osmotic pressure of body fluids (about 7.5 atm). Sodium chloride is an especially effective osmotic solute in that the osmotic pressure of sodium chloride is sufficiently high to remove the dependence of pumping rate on the osmotic pressure of the surrounding environment.

The polymer vehicle serves to make the osmotically effective composition thermoformable. The thermoformability of the composition permits sleeve layer 13 to be produced by conventional thermoforming techniques such as compression molding, injection molding, or extrusion. A preferred water soluble, thermoplastic polymer vehicle is a mixture of about 40% to about 70% by weight poly(ethylene oxide) having a molecular weight in the range of about 100,000 to about 4,000,000 and about 30% to about 60% by weight poly(ethylene glycol) having a molecular weight in the range of about 1,000 and about 30,000. The cellulose 2-hydroxypropyl ethers sold by Hercules, Inc. under the mark KLUCEL may also be used as the polymer vehicle.

In addition to the solute and vehicle, the osmotically effective solute composition may contain minor amounts of other materials such as fillers, pigments, lubricants, and other conventional additives that facilitate thermoforming.

Sleeve layer 13 is encapsulated by outer membrane 12. Membrane 12 also covers the exterior of the portion of bag 14 above shoulder 24 and forms a fluid tight seal therewith. At least a part of membrane 12 is permeable to water. Membrane 12 is substantially impermeable to the osmotically effective solute composition. Membrane 12 is also shape-retaining, that is, it is sufficiently rigid to be substantially undeformed by the hydrostatic pressure that is generated in the space between its inner surface and the exterior of bag 14 by the water imbibed by the solute of sleeve 13. The thickness and composition of membrane 12 affects the rate at which water will be imbibed through it by the solute in sleeve 13. Such membranes and compositions that may be used to form them include cellulose acetates, cellulose acetate butyrates, and other shape-retaining semipermeable membranes including those disclosed in said U.S. Pat. No. 3,760,984 at col. 4, line 53 to col. 5, line 39 and in said U.S. Pat. No. 3,995,631 at col. 7, line 40 to col. 8, line 15, which disclosures are incorporated herein by reference.

Plug 15 fits into the open end 22 of bag 14. Plug 15 is generally cylindrical and is approximately as long as the thickened portion of bag 14 above shoulder 24. The exterior of plug 15 forms a fluid tight seal with the portion of the interior surface of bag 14 with which it is in contact. Plug 15 is comprised of a material that is substantially impermeable to composition 18. Accordingly, plug 15 is provided with an axial, central filling-/discharge port 25 extending completely through it. Port 25 provides access to the interior of bag 14 for filling bag 14 with active agent composition 18 and dispensing composition 18 therefrom.

Port 25 can be adapted to receive flow moderator 16 as shown in FIG. 7. Plug 15 has a hemispherically shaped recess 26 in its inner (bottom) end 27. The presence of such a recess or concavity in end 27 reduces the likelihood of entrapping air in bag 14 when filling bag 14 with composition 18. In prior versions of the mini-osmotic pump this plug has been generally cylindrical in shape, its inner end joining the wall of the bag at a 90° angle (see, for example, U.S. Pat. No. 3,987,790). During the filling of the bag, the fluid has a natural tendency, due to its high surface tension, to form a curved surface beginning near the top of the wall of the bag and continuing up to the filling/discharge port. This curvature causes an air pocket to form at the intersection of the wall of the bag and the plug. The preferred plug has a hemispherically recessed lower surface, curved to substantially match the arc created by the surface tension of the drug solution during the filling process. This also reduces the volume of the dispenser which cannot be filled due to air entrapment. Plug 15 may be made from the same materials as are used to make flexible bag 14; however, the dimensions of plug 15 should be such that it is substantially inflexible.

Flow moderator 16 provides the passageway from the interior of bag 14 to the exterior of dispenser 11 by which composition 18 is discharged from dispenser 11. Flow moderator 16 comprises a conduit, in the form of a rigid cylindrical tube 28, and a dome-shaped head 29. Tube 28 and head 29 may be made from suitable plastics or metals. Head 29 has an axial, threaded bore 32 that receives threaded end 33 of tube 28. As shown in FIG. 7, end 33 extends outwardly from the spherical surface of head 29 to provide a site for attaching an external catheter tube (not shown) in the event dispenser 11 is to be used to administer composition 18 to a remote location. The outer diameter of tube 28 is approximately the same as the diameter of port 25 such that tube 28 may be inserted through port 25 into bag 14 with tube 28 fitting snugly within port 25 so as to form an essentially fluid tight seal with plug 15. The length of tube 28 is preferably such that it extends into bag 14 to at least about 50% of the elongated dimension of the interior of bag 14, i.e., the distance from the inner side of end 19 to end 27 of plug 15. More preferably, tube 28 extends into bag 14 over about 85% to 95% of said elongated dimension. The inner diameter of tube 28 is correlated to the length of tube 28 such that substantial diffusional flow of composition 18 through tube 28 will not occur. Tube 28 is, in effect, a capillary that provides resistance to the flow of composition 18, thereby reducing or eliminating bulk loss of composition 18, from the outlet port of dispenser 11. Head 29 has a diameter slightly greater than the outer diameter of plug 15. As seen in FIG. 2, the flat side of head 29 fits against the top of plug 15.

Dispenser 11 may be filled with fluid 18 via port 25 of plug 15. For instance, the needle of a fluid loaded syringe may be inserted through port 25 and the syringe contents discharged into bag 14. To insure that a predetermined fluid pumping rate is achieved, it is desirable to completely fill bag 14 with fluid 18. After the bag is filled, tube 28 of flow moderator 16 is inserted through port 25 to the position shown in FIG. 7. As described above, tube 28 functions as a capillary and inhibits loss of fluid 18 even when the dispenser 11 is subjected to substantial movement or tipped upside down.

Flow moderator cap 17 may be used to cover protruding end 33 of tube 29 when dispenser 11 is used without an external catheter tube connection. Cap 17 is crescent-shaped and has an axial threaded bore 34 that receives end 33 of tube 29. The curvature of its concave underside 35 matches the convexity of the top surface of head 29 so that the former fits tightly against the latter (FIG. 7). The outer diameter of cap 17 is substantially the same as the outer diameter of slidable outer cover 43. Thus the hemispherical exterior of cap 17 provides a smooth blunt surface that aligns with the exterior surface of outer cover 43.

The components of dispenser 11 may be made and assembled as follows. Bag 14 and sleeve 13 are thermoformed, such as by known injection molding techniques. The bag-sleeve subassembly may be made using solvent or adhesive bonding, depending on the material involved. If bag 14 and sleeve layer 13 are capable of being solvent bonded, bag 14 is dipped in the mutual solvent and inserted into sleeve layer 13. When the subassembly is put together by adhesive bonding, bag 14 is dipped into an appropriate adhesive and then inserted into sleeve layer 13. Membrane 12 may be applied to the bag-sleeve subassembly by dipping it in a solution of membrane material as taught in U.S. Pat. No. 3,987,790 at col. 4, line 63 or membrane 12 may be coated onto the subassembly using conventional coating equipment and techniques such as pan coating and fluidized spray coating.

When the wicking layer 42 is formed of a hydrophilic cellulose acetate material, wicking layer 42 can likewise be coated onto the exterior of membrane 12 using conventional coating equipment and techniques such as dip coating, pan coating and fluidized spray coating. In the case where the wicking layer comprises a cellulose filter paper-like material, the layer is typically preformed into the appropriate sleeve shape and then slipped over the membrane 12 where it may be retained by a friction fit or a hydrophilic glue. The outer sleeve 43 is typically formed by injection molding of the semipermeable membrane polymers optionally with a hydrophilic flux enhancer.

Referring now to FIGS. 5 and 6, there is shown an alternate embodiment of the present invention. Referring first to FIG. 5, there is shown a dispenser 111 prior to introduction into an aqueous environment, and thus the water-swellable composition 144 is in a non-expanded condition. The components of dispenser 111 include an end plug 115 having an axially extending passageway 125 therethrough. End plug 115 is comprised of an impermeable material such as plastic and the like. End plug 115 mates with a tubular semipermeable membrane 112. The end plug 115 and the membrane 112 define an interior space filled with an osmotically active composition 118. Composition 118 may be, for example, a mixture of a drug or other beneficial agent together with an osmotically effective solute in solid or liquid form, such as sodium chloride or the like.

The combination of plug 115 and the shape-retaining semipermeable membrane 112 containing composition 118 comprise a mini-osmotic pump of the type known in the prior art. The improved mini-osmotic pump of the present invention further includes the following components: a wicking layer 142; a displaceable outer cover 143 including a portion 147 adjacent the wicking layer 142 and a semipermeable or microporous end portion 145 adjacent composition 144; and a water-swellable composition 144 positioned between the end portion 145 and the lower end of the mini-osmotic pump.

Dispenser 111 operates in a similar manner to dispenser 11. Once placed in an aqueous environment, such as within a body cavity or within body tissue, water from the environment is imbibed by the water-swellable composition 144 through semipermeable/microporous portion 145 of cover 143. As the composition 144 absorbs water, it begins to swell. Since the cover 144 is shape-retaining, the swelling of composition 144 displaces the outer cover 143, causing it to slide over the wicking layer 142. Preferably, the portions of cover 143 immediately adjacent the wicking layer 142 are water impermeable so that during the period of time in which composition 44 is absorbing water and swelling, the wicking layer remains completely dry. Eventually, the composition 144 swells a sufficient amount to break the seal provided by the wax plug 146 and expose a portion 150 of wicking layer 142 to the aqueous environment, as is illustrated in FIG. 6. Once exposed, the wicking layer 142 wicks water to substantially the entire surface of membrane 112. Water from the wicking layer 142 is imbibed by the solute in composition 118 through membrane 112 at a rate determined by the osmotic activity of the solute, the osmotic reflection coefficient, and the composition, thickness, and wetted area of membrane 112. The imbibed water dissolves the solute in composition 118. As more water permeates through membrane 112, the solution, together with any drug or other beneficial agent, is pumped out of passageway 125.

The following example is intended to further illustrate the above described dispenser and its manufacture. This example is not intended to limit the invention in any way.

EXAMPLE

A cylindrical flexible bag (reference numeral 14 in FIG. 1) having the following dimensions (2.50 cm long, 4.01 mm I.D. and 4.62 mm O.D.) is injection molded at 176° C., $3.5 \times 10^3$ kPa, from an elastomeric styrene-butadiene copolymer (sold under the trade designation, Kraton 2104).

An osmotic sleeve (reference numeral 13 in FIG. 1) is prepared as follows. The components (64.5 wt. % NaCl, 20 wt. % poly[ethylene oxide], molecular wt 600,000, 15 wt. % poly[ethylene glycol] of molecular weight 20,000 and 0.5 wt. % colloidal $SiO_2$, sold under the trade name Cabosil are bulk blended in a Hobart mixer for 20 minutes at low speed. The homogenous powder blend is pressed into 0.6 cm tablets capable of being gravity fed into Arborg injection molding equipment. The osmotic sleeve (2.21 cm long, 4.87 mm I.D., and 5.89 mm O.D.) is formed from the tablets by injection molding at 149° C. and $6.5 \times 10^3$ kPa.

A cylindrical plug of the above described styrene-butadiene copolymer is injection molded. The plug is 0.5 cm long, has a 4.1 mm O.D., the lower surface is recessed hemispherically to a depth of 1.37 mm, and has a central axial port 0.76 mm in diameter through the length of the plug. The cylindrical flexible bag is dipped into a 15 wt. % cyclohexane solution of the styrene-butadiene copolymer mentioned above and is inserted into the osmotic sleeve. The arcuate surfaces of the plug are coated with a glue bead of 15 wt. % cyclohexane solution of the copolymer and the plug is inserted into the open end of the bag.

A semipermeable membrane (reference numeral 12 in FIG. 1) is applied to the dispenser by coating with a Wurster coater. The membrane is formed from a 4 wt. % methylene chloride solution of cellulose acetate butyrate (sold under the designation Eastman Kodak 381-2). The coating is applied to a thickness of 0.38 mm. The dispenser is then oven-dried at 55° C. for about 5-10 days.

A semipermeable outer cover (reference numeral 43 in FIG. 1) is formed by injection molding cellulose acetate. The cellulose acetate has an acetyl content of 39.8%, is plasticized with 32% triacetin and contains 20% polyvinyl pyrrolidone as a flux enhancer. The molded sleeve has a wall thickness of 10 mils and an external diameter of 0.85 cm.

A wicking layer (reference numeral 42 in FIG. 1) formed of a cotton gauze material is wrapped around the semipermeable membrane of the dispenser. The wicking layer is applied to the exterior of the membrane using a hydrophilic glue.

A water-swellable polymer tablet (reference numeral 44 in FIG. 1) is formed having the following dimensions (0.8 cm diameter; 0.4 cm height). The tablet is formed from about 200 mg of a polymer blend comprising 4 parts by weight of polyox coagulant (m.w. of 5,000,000) and 1 part by weight of carbopol 934 p (m.w. of 3,000,000). The water-swellable tablet is formed by compressing the water-swellable polymer in a conventional tablet making machine. The water-swellable tablet is then placed in the bottom of the semipermeable outer sleeve. The outer sleeve is then slid over the semipermeable membrane of the dispenser until all of the semipermeable membrane and wicking layer is covered by the outer sleeve. The annular space between the open end of the outer sleeve and the plug of the dispenser is sealed using an annular plug of sealing wax having a length of about 3 mm.

A flow moderator is prepared for the dispenser as follows. Twenty-one gauge needle stock is cut into a 2.36 cm length. The length of tubing is circumferentially grooved with 15 grooves, equally spaced 0.3 mm apart along one end of the tube, such that a 4.3 mm distance beginning at one end of the tube is grooved. A cap formed of styreneacrylonitrile copolymer is insert molded around the grooved portion of the tube 3 mm from the grooved end. The cap is hemispherical, 5.6 mm in diameter, with a 0.8 mm diameter diametrical bore. A hemispherical overcap having a 6.5 mm O.D., is 4.3 mm in length with the bottom hemispherically recessed to a depth of 1.3 mm, has a 0.8 mm diameter diametrical bore through the length of the overcap, and is injection molded from ethylene-vinyl-acetate copolymer. The overcap is pressed onto the 3 mm grooved extension of the tube.

The flexible bag is then filled with a blue liquid dye. The liquid dye is introduced into the flexible bag using a hypodermic needle inserted through the central axial port in the plug. The mini-osmotic pump is then placed in a 100 ml beaker filled with distilled water and observed to measure the initial activation period (i.e., the length of time between placing the pump in the beaker and the time when the dye begins to be dispensed from the pump). During the activation period, distilled water permeates through the outer cover and is absorbed by the water swellable tablet. This causes the tablet to swell, eventually displacing the sleeve and exposing the wicking layer which in turn activates the dispenser, as evidenced by the pumping of dye solution therefrom. It is found that, on average, the dispenser begins pumping dye into the water after a delay of approximately four hours.

We claim:
1. An osmotically driven fluid dispenser comprising:
   (a) a shaped membrane defining a compartment, the compartment containing an osmotically effective solute composition, said membrane being at least in part permeable to water and having a port from which a solution of the solute may be dispensed from the compartment;
   (b) a cover sealing the membrane from an exterior aqueous environment, at least a portion of the cover being comprised of a material selected from the group consisting of semipermeable and microporous materials;
   (c) a wicking layer positioned between the membrane and the cover and sealed within the cover; and
   (d) a water swellable composition operatively positioned within the cover, wherein said water-swellable composition is capable of absorbing water which passes through the material, expanding over a predetermined activation period, displacing the membrane relative to the cover and thereby exposing the wicking layer and the membrane to the aqueous environment.

2. The dispenser of claim 1, wherein the wicking layer comprises a fabric containing cellulosic fibers.

3. The dispenser of claim 2, wherein the wicking layer is attached to the membrane by means of a hydrophilic glue.

4. The dispenser of claim 1, wherein the wicking layer is comprised of cellulose acetate.

5. The dispenser of claim 4, wherein the wicking layer is coated on the membrane.

6. The dispenser of claim 1, wherein the water-swellable composition comprises polyethylene oxide having a molecular weight in the range of about 100,000 to about 4,000,000.

7. The dispenser of claim 6, wherein the polyethylene oxide is cross-linked.

8. The dispenser of claim 1, wherein the cover is comprised at least in part of a polymer that is permeable to water and substantially impermeable to the water-swellable composition.

9. The dispenser of claim 8, wherein the polymer is selected from the group consisting of polymers of cellulose acetate and cellulose butyrate.

10. The dispenser of claim 1, wherein the predetermined activation period is in the range of up to about 18 hours.

11. The dispenser of claim 1, wherein the activation period is in the range of about 3 to about 12 hours.

12. An osmotically driven fluid dispenser comprising:
   (a) an inner flexible bag adapted to contain the fluid;
   (b) an intermediate layer of an osmotically effective solute composition at least partly encapsulating the bag;
   (c) a shape-retaining membrane encapsulating the layer of osmotically effective solute composition, said membrane being at least in part permeable to water;
   (d) a port that extends from the interior of the bag to the exterior of the dispenser through which the fluid may be charged into the bag and dispensed from the bag;
   (e) a cover sealing the membrane from an exterior aqueous environment, at least a portion of the cover being comprised of a material selected from the group consisting of semipermeable and microporous materials;
   (f) a wicking layer positioned between the membrane and the cover and sealed within the cover; and
   (g) a water-swellable composition operatively positioned within the cover, wherein said water-swellable composition is capable of absorbing water which passes through the material, expanding over a predetermined activation period, displacing the cover and thereby exposing the wicking layer and the membrane to the aqueous environment.

13. The dispenser of claim 12, wherein the wicking layer comprises a fabric containing cellulosic fibers.

14. The dispenser of claim 13, wherein the wicking layer is attached to the membrane by means of a hydrophilic glue.

15. The dispenser of claim 12, wherein the wicking layer is comprised of cellulose acetate.

16. The dispenser of claim 15, wherein the wicking layer is coated on the membrane.

17. The dispenser of claim 12, wherein the water-swellable composition comprises polyethylene oxide having a molecular weight in the range of about 100,000 to about 4,000,000.

18. The dispenser of claim 17, wherein the polyethylene oxide is cross-linked.

19. The dispenser of claim 12, wherein the cover is comprised at least in part of a polymer that is permeable to water and substantially impermeable to the water-swellable composition.

20. The dispenser of claim 19, wherein the polymer is selected from the group consisting of polymers of cellulose acetate and cellulose butyrate.

21. The dispenser of claim 12, wherein the dispensed fluid comprises a drug that produces a local or systemic physiologic or pharmacologic response in an animal.

22. The dispenser of claim 21, wherein the animal is a human.

23. The dispenser of claim 12, wherein the dispenser has a size and shape adapting it to be swallowed by an animal.

24. The dispenser of claim 12, wherein the dispenser has a size and shape adapted it to be implanted in an animal.

25. The dispenser of claim 12, wherein the predetermined activation period is in the range of up to about 18 hours.

26. The dispenser of claim 25, wherein the activation period is in the range of about 3 to about 12 hours.

27. A method of activating an osmotically driven fluid dispenser in an aqueous environment after a predetermined activation period, the dispenser including a shaped membrane defining a compartment, the compartment containing an osmotically effective solute composition, said membrane being at least in part permeable to water, the dispenser having a port from which a solution of the solute may be dispensed from the compartment comprising:
(a) sealing the membrane within a cover which is comprised at least in part of a material selected from the group consisting of semipermeable and microporous materials;
(b) positioning a water-swellable composition within the cover, said water-swellable composition being capable of absorbing water which passes through the material and expanding over the predetermined activation period in response thereto;
(c) positioning a wicking layer between the membrane and the cover, the wicking layer being sealed within the cover; and
(d) exposing the cover to an aqueous environment, whereby said water-swellable composition absorbs water from the environment, expands and displaces the cover, thereby exposing the wicking layer and the membrane to the aqueous environment and activating the dispenser.

28. The method of claim 27, wherein at least a portion of the wicking layer is exposed to an aqueous exterior environment after the water-swellable composition displaces the cover.

29. The method of claim 28, wherein the exposed portion of the wicking layer wicks water to the membrane.

30. The method of claim 27, wherein the predetermined activation period is in the range of up to about 18 hours.

31. The method of claim 27, wherein the activation period is in the range of about 3 to about 12 hours.

32. A method of activating an osmotically driven fluid dispenser in an aqueous environment after a predetermined activation period, the dispenser including an inner flexible bag adapted to contain the fluid, an intermediate layer of an osmotically effective solute composition at least partly encapsulating the bag, a shape-retaining membrane encapsulating the layer of osmotically effective solute composition, said membrane being at least in part permeable to water, and a port that extends from the interior of the bag to the exterior of the dispenser through which the fluid may be charged into the bag and dispensed from the bag, comprising:
(a) sealing the membrane within a cover which is comprised at least in part of a material selected from the group consisting of semipermeable and microporous materials;
(b) positioning a water-swellable composition within the cover, said water-swellable composition being capable of absorbing water which passes through the material and expanding over the predetermined activation period in response thereto;
(c) positioning a wicking layer between the membrane and the cover, the wicking layer being sealed within the cover; and
(d) exposing the cover to an aqueous environment, whereby said water-swellable composition absorbs water, expands and displaces the cover, thereby exposing the wicking layer and the membrane to the aqueous environment and activating the dispenser.

33. The method of claim 32, wherein at least a portion of the wicking layer is exposed to an aqueous exterior environment after the water-swellable composition displaces the cover.

34. The method of claim 33, wherein the exposed portion of the wicking layer wicks water to the membrane.

35. The method of claim 32, wherein the predetermined activation period is in the range of up to about 18 hours.

36. The method of claim 32, wherein the activation period is in the range of about 3 to about 12 hours.

37. The method of claim 32, wherein the aqueous environment is within an animal body.

38. The method of claim 37, wherein the animal is a human.

* * * * *